United States Patent
Galow

(10) Patent No.: US 10,864,149 B2
(45) Date of Patent: Dec. 15, 2020

(54) NON-AEROSOL SHAVING COMPOSITIONS

(71) Applicant: Edgewell Personal Care Brands, LLC., Chesterfield, MO (US)

(72) Inventor: Peter Galow, Lagenfeld (DE)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 0 days.

(21) Appl. No.: 15/557,340

(22) PCT Filed: Mar. 23, 2016

(86) PCT No.: PCT/US2016/023719
§ 371 (c)(1),
(2) Date: Sep. 11, 2017

(87) PCT Pub. No.: WO2016/154275
PCT Pub. Date: Sep. 29, 2016

(65) Prior Publication Data
US 2018/0104165 A1    Apr. 19, 2018

Related U.S. Application Data

(60) Provisional application No. 62/136,749, filed on Mar. 23, 2015.

(51) Int. Cl.
| | | |
|---|---|---|
| A61K 8/36 | (2006.01) | |
| A61K 8/39 | (2006.01) | |
| A61Q 9/02 | (2006.01) | |
| A61K 8/81 | (2006.01) | |
| A61K 8/04 | (2006.01) | |

(52) U.S. Cl.
CPC .............. *A61K 8/361* (2013.01); *A61K 8/046* (2013.01); *A61K 8/39* (2013.01); *A61K 8/8176* (2013.01); *A61Q 9/02* (2013.01); *A61K 2800/30* (2013.01); *A61K 2800/87* (2013.01)

(58) Field of Classification Search
CPC ............ A61K 2800/30; A61K 2800/87; A61K 8/046; A61K 8/361; A61K 8/39; A61K 8/8176; A61Q 9/02
See application file for complete search history.

(56) References Cited

U.S. PATENT DOCUMENTS

| | | | | |
|---|---|---|---|---|
| 2006/0134095 A1* | 6/2006 | Ito | ............................. | A61K 8/19 424/125 |
| 2009/0053161 A1* | 2/2009 | Nguyen | ................... | A61K 8/39 424/70.17 |
| 2009/0169502 A1* | 7/2009 | Quadir | ..................... | A61K 8/36 424/70.9 |

FOREIGN PATENT DOCUMENTS

| | | | | |
|---|---|---|---|---|
| DE | 102004027323 A1 * | 12/2005 | ............. | A61K 8/361 |
| WO | 2009101583 A1 | 8/2009 | | |
| WO | 2011103173 A2 | 8/2011 | | |
| WO | 2012084970 A1 | 6/2012 | | |
| WO | WO-2012084970 A1 * | 6/2012 | ............. | A61Q 19/10 |
| WO | WO-2016102395 A1 * | 6/2016 | ............... | A61K 8/60 |

OTHER PUBLICATIONS

WO-2012084970-A1, Espacenet English translation, downloaded Dec. 2019 (Year: 2019).*
International Search Report issued in connection with corresponding application No. PCT/US2016/023719 dated May 11, 2016.

* cited by examiner

*Primary Examiner* — Mark V Stevens

(57) ABSTRACT

The present invention relates to non-aerosol shaving compositions which are free of propellants, and methods of preparing and using such shaving composition. In particular, the present invention relates to a non-aerosol, propellant-free composition comprising:
(i) at least two $C_{14}$ to $C_{16}$ carboxylic acids or an alkali metal salt thereof;
(ii) at least one compound of general Formula (I)

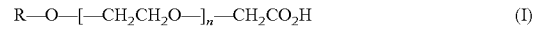

$$R-O-[-CH_2CH_2O-]_n-CH_2CO_2H \qquad (I)$$

or an alkali metal salt thereof,
wherein
R represents a saturated, straight- or branched-chain $C_{10}$ to $C_{18}$ alkyl group; and
n represents an integer between 4 and 12;
(iii) polyvinyl pyrrolidone; and
(iv) water.

29 Claims, No Drawings

NON-AEROSOL SHAVING COMPOSITIONS

This application is the National Phase of International Application No. PCT/US16/23719, filed on Mar. 23, 2013, the entirety of which is incorporated herein for reference.

TECHNICAL FIELD

The present invention relates to shaving compositions which are free of propellants, methods of preparing said compositions and shaving foams comprising said compositions.

BACKGROUND ART

Shaving foam constitutes a product which has been used widely across the global marketplace for more than fifty years for the preparation of hairs of all varieties, and in particular beard hairs, for convenient removal. Shaving foam can be obtained from a number of different formulae including shaving soap bars and bowls, shaving preparation pastes, aerosol shaving foams and post-foaming gels, of which the latter two constitute the most common formulations used at present.

Shaving foams typically comprise a number of ingredients, including soap-based formulae (organic acids) or non-soap tensides (surfactants) in combination with neutralizers, stabilizers, scents and often other skin care ingredients. In addition to performance which is delivered through these ingredients, certain additional properties are expected by the consumer. In this regard, foaming ability is a characteristic of particular relevance for commercial success. Accordingly, in addition to the common ingredients required for performance, commercially successful post-foaming gels and aerosol shaving foams exhibit the additional presence of an often flammable propellant in order to, inter alia, enable the formation of the desired white and creamy foam.

One consequence of the presence of propellants in shaving foam compositions is the requirement that they be packaged in pressure-resistant containers, often taking the form of tin-plated steel or aluminum cans which are sealed closed by means of a male-female valve. The valve is then equipped with a foam head (actuator) and cap which allows for safe transport.

The necessity that pressure-resistant containers be used adds a number of additional complications to the manufacturing and distribution processes of the final shaving composition product, which often bring with them additional financial repercussions. In this regard, manufacturing facilities possessing explosion-proof areas, special equipment for the storage of raw materials (especially for flammable gases), special equipment for can-filling and package assembly, the necessity for safety testing and the additional logistical complications associated with the finished goods (classified as dangerous goods) all act to render the finished product substantially more expensive than if propellants were not to be present in the composition.

A common disadvantage of non-aerosol shaving compositions has been that they fail to mirror some of the aesthetic characteristics of propellant-containing shaving compositions. Although not necessarily inferior in terms of performance, foams which lack such characteristics are often deemed less attractive by the consumer, and thus, can suffer a commercial disadvantage when compared to propellant-containing shaving compositions. Of particular importance in this respect is the ability of the shaving composition to form the fine-pored, white and creamy foam composition desired by consumers. Other characteristics sought by consumers in shaving compositions include lubriciousness, cushion, and skin feel. Due to the absence of propellant in propellant-free shaving compositions, it is desirable that a fine-pored, white, creamy foam be furnished simply upon rubbing the composition against the skin. In such cases, atmospheric air constitutes the gaseous component of the foam. It is furthermore desirable that the resultant foam persists for the complete duration of the shave, i.e., foam stability must be comparable to that of propellant-containing compositions, and that any residual foam must be capable of being easily washed from the skin and razor, thus leaving no residues upon running water through the blades.

A number of attempts to develop propellant-free foam and gel shaving compositions which display characteristics common with analogous propellant-containing products have been reported in the prior art.

JPH 08131809 discloses a non-gas foamed composition which incorporates N-long-chain acyl-[alpha]-amino acids or their salts and is suitable for application in numerous detergent and cosmetic applications including shaving foam compositions.

U.S. Pat. No. 5,340,571 discloses a non-aerosol aqueous shaving composition constituting a sarcosinate and hydroxyethylcellulose in the form of clear shaving preparation.

WO 2003/009823 is directed to a non-aerosol shaving composition in the form of a gel comprising water, an alkanolamine soap and a solubilizing agent for the soap, wherein the soap is completely dissolved in the water and the amount of soap and solubilizing agent is sufficient to provide the soap ire the hexagonal liquid crystal phase in the composition.

EP 1739161 describes the provision of high concentration aqueous solutions of alkyl ether carboxylates which remain pumpable and are used as foam-enhancing agents to deliver foams with satisfactory properties including foaming ability, foam stability, creaminess of the foam, foam density and foam speed.

WO 2012/084970 relates to foamable cosmetic compositions for skin and body care which are foamed using fluorocarbon or hydrofluorocarbon propellants as foaming agents. In addition to propellants, these compositions comprise 10 to 97 wt. % water, 0.1 to 30 wt. % of at least two tenside and at least two cosmetic conditioning agents selected from separate conditioning agent classes as essential features.

To date, the best non-aerosol shaving compositions have proven incapable of satisfying all of the criteria which would render them equally as attractive to the consumer as propellant-containing shaving compositions. For example, non-aerosol shaving compositions have only proven capable of furnishing foams with characteristics typically acceptable to the consumer in preparations intended for hand washing, the ability to form the fine-pored, rich, creamy foam expected by consumers proving to date an unobtainable characteristic. Moreover, in comparison with propellant-containing compositions, their foams often exhibit inferior and inadequate water retention properties, which requires that the skin be wet before application of the shaving composition. The provision of a non-aerosol shaving composition, which is capable of generating a foam which meets the characteristics demanded by the consumer both in terms of performance as well as physical/aesthetic properties has remained elusive.

Accordingly, it has been an object of the present invention to furnish a non-aerosol shaving composition which is capable of generating a foam which meets the performance and physical/aesthetic characteristics demanded by the consumer whilst simultaneously overcoming the above-outlined disadvantages associated with propellant-containing shaving compositions.

SUMMARY OF THE INVENTION

The present invention solves the problem of providing a non-aerosol shaving composition showing good foamability which is capable of generating a stable, voluminous foam upon rubbing against the skin and which provides good skin feel, good water retention, lubriciousness, good cushion, leaves substantially no residues upon running water through the blades of the razor, and whose foam stability leads to the foam persisting during the entire duration of the shave.

DETAILED DESCRIPTION OF THE INVENTION

The embodiments of the present invention can comprise, consist of, and consist essentially of the features and/or steps of the invention described herein, as well as any of the additional or optional ingredients, components, steps, or limitations described herein or would otherwise be appreciated by one of skill in the art. It is to be understood that all concentrations disclosed herein are by weight percent (wt. %) based on a total weight of the entire composition unless otherwise indicated.

Definitions

As used in the present application, the term 'propellant' refers to any material capable of being used as a vehicle for expelling the shaving composition from a container without the application of external force from, for example, a pump or other mechanical expulsion mechanism. As used herein, the term 'propellant' also refers to materials commonly used as blowing agents or post-foaming gel agents in the field of cosmetics, the identity of which are known to the person skilled in the art. Accordingly, these terms can be used interchangeably in the present application. However, air or compressed air is not included in the term "propellant".

The term 'entire composition' as used herein refers to the composition obtained in any given embodiment by combining each of components (i) to (iv) as defined above as well as any of the optional additional agents as defined above, any of the optional additional ingredients as defined above as required for the specific embodiment and any other components present.

INCI names are names assigned to specific ingredients used in cosmetics and personal care compositions named under the International Nomenclature of Cosmetic Ingredient system and the identities of components labeled with this nomenclature are thus readily understood and recognized by the person skilled in the art.

All measurements and determinations have been carried out at room temperature (21° C.±1° C.) unless otherwise stated.

Component (i)

The present invention relates to a non-aerosol shaving composition. The non-aerosol shaving composition of the present invention comprises at least two $C_{12}$ to $C_{18}$ carboxylic acids or alkali metal salts thereof. The at least two $C_{12}$ to $C_{18}$ carboxylic acids can be straight-chain carboxylic acids, branched-chain carboxylic acids, or combinations thereof. In some embodiments of the present invention, the at least two $C_{12}$ to $C_{18}$ carboxylic acids are straight-chain fatty acids. In some embodiments of the present invention, the at least two $C_{12}$ to $C_{18}$ carboxylic acids are branched chain fatty acids. In some embodiments of the present invention, the at least two $C_{12}$ to $C_{18}$ carboxylic acids are saturated fatty acids. In some embodiments of the present invention, the at least two $C_{12}$ to $C_{16}$ carboxylic acids are saturated, branched-chain fatty acids. In some embodiments of the present invention, the at least two $C_{12}$ to $C_{18}$ carboxylic acids are saturated, straight-chain fatty acids.

In some embodiments of the present invention, the at least two $C_{12}$ to $C_{18}$ carboxylic acids of the present invention are $C_{14}$ or $C_{18}$ straight-chain carboxylic acids. In some embodiments of the invention the at least two $C_{14}$ to $C_{18}$ carboxylic acids of the present invention are straight-chain carboxylic acids. In some embodiments, the at least two $C_{14}$ or $C_{18}$ carboxylic acids of the present invention are selected from the group consisting of myristic acid, palmitic acid, stearic acid, and combinations thereof. In some embodiments of the present invention the at least two $C_{14}$ to $C_{18}$ carboxylic acids are myristic acid in combination with palmitic acid. In some embodiments of the present invention the at least two $C_{14}$ to $C_{18}$ carboxylic acids are myristic acid in combination with stearic acid. In some embodiments of the present invention, the at least two $C_{14}$ to $C_{18}$ carboxylic acids are a combination of myristic acid, palmitic acid, and stearic acid.

When the at least two $C_{14}$ to $C_{18}$ carboxylic acids is a combination of a $C_{14}$ carboxylic acid and a $C_{16}$ carboxylic acid, the ratio of the $C_{14}$ carboxylic acid to the $C_{16}$ carboxylic acid may vary. In some embodiments the ratio of the $C_{14}$ carboxylic acid to the $C_{16}$ carboxylic acid is from 5:1 to 1:5. In some embodiments the ratio of the $C_{14}$ carboxylic acid to the $C_{16}$ carboxylic acid is from 3:1 to 1:3. In some embodiments the ratio of the $C_{14}$ carboxylic acid to the $C_{16}$ carboxylic acid is from 2:1 to 1:2. In some embodiments the ratio of the $C_{14}$ carboxylic acid to the $C_{16}$ carboxylic acid is 1:1.

When the at least two $C_{14}$ to $C_{18}$ carboxylic acids is a combination of a $C_{14}$ carboxylic acid and a $C_{18}$ carboxylic acid, the ratio of the $C_{14}$ carboxylic acid to the $C_{18}$ carboxylic acid may vary. In some embodiments the ratio of the $C_{14}$ carboxylic acid to the $C_{18}$ carboxylic acid is from 5:1 to 1:5. In some embodiments the ratio of the $C_{14}$ carboxylic acid to the $C_{18}$ carboxylic acid is from 3:1 to 1:3. In some embodiments the ratio of the $C_{14}$ carboxylic acid to the $C_{18}$ carboxylic acid is from 2:1 to 1:2. In some embodiments the ratio of the $C_{14}$ carboxylic acid to the $C_{18}$ carboxylic acid is 1:1.

When the at least two $C_{14}$ to $C_{18}$ carboxylic acids is a combination of a $C_{16}$ carboxylic acid and a $C_{18}$ carboxylic acid, the ratio of the $C_{16}$ carboxylic acid to the $C_{18}$ carboxylic acid may vary. In some embodiments the ratio of the $C_{14}$ carboxylic acid to the $C_{18}$ carboxylic acid is from 5:1 to 1:5. In some embodiments the ratio of the $C_{14}$ carboxylic acid to the $C_{18}$ carboxylic acid is from 3:1 to 1:3. In some embodiments the ratio of the $C_{14}$ carboxylic acid to the $C_{18}$ carboxylic acid is from 2:1 to 1:2. In some embodiments the ratio of the $C_{14}$ carboxylic acid to the $C_{18}$ carboxylic acid is 1:1.

When the at least two $C_{14}$ to $C_{18}$ carboxylic acids is a combination of a $C_{14}$ carboxylic acid, a $C_{15}$ carboxylic acid, and a $C_{15}$ carboxylic acid, the ratio of the $C_{14}$ carboxylic acid to the $C_{16}$ carboxylic acid to the $C_{18}$ carboxylic acid may vary. In some embodiments the ratio of the $C_{14}$ carboxylic acid to the $C_{16}$ carboxylic acid to the $C_{18}$ carboxylic acid is 1:1:1.

In some embodiments of the present invention, the non-aerosol shaving composition which comprises (i) at least two $C_{14}$ to $C_{18}$ carboxylic acids or alkali metal salts thereof, comprises no additional fatty acids of different chain length or alkali metal salts thereof except for those defined as a compound of Formula (I) below. For example, in some embodiments of the present invention myristic acid and palmitic acid are the only $C_{14}$ to $C_{18}$ carboxylic acids present in the entire non-aerosol shaving composition, and in some embodiments myristic acid and stearic acid are the only fatty acids present in the entire non-aerosol shaving composition.

In the non-aerosol shaving composition of the present invention, the at least two $C_{14}$ to $C_{18}$ carboxylic acids may be present as an alkali metal salt thereof. The alkali metal is selected from the group consisting of lithium, sodium and potassium. In some embodiments the alkali metal is sodium or potassium.

In some embodiments of the present invention, the at least two $C_{14}$ to $C_{18}$ carboxylic acid or alkali metal salt thereof is present in an amount of 1.0 wt. % or more to 10.0 wt. % or less based on the weight of the entire composition. In some embodiments of the present invention, the at least two $C_{14}$ to $C_{16}$ carboxylic acids or alkali metal salts thereof is present in an amount of 1.0 wt. % or more to 7.5 wt. % or less based on the weight of the entire composition. In some embodiments of the present invention, the at least two $C_{14}$ to $C_{16}$ carboxylic acid or alkali metal salt thereof is present in an amount of 1.25 wt. % or more to 5.0 wt. % or less based on the weight of the entire composition.

Component (ii)

The non-aerosol shaving composition of the present invention further comprises at least one compound of Formula (I):

$$R\text{—}O\text{—}[\text{—}CH_2CH_2O\text{—}]_n\text{—}CH_2CO_2H \qquad (I)$$

or an alkali metal salt thereof.

In the at least one compound of Formula (I) or the alkali metal salt thereof, n represents an integer between 4 and 12. In some embodiments of the invention, n is from or more to 11 or less. In some embodiments, n is 5, 6, 8 or 11. In some embodiments, n is 6.

In the at least one compound of Formula (I) or the alkali metal salt thereof, R represents a straight- or branched-chain, saturated $C_{10}$ to $C_{18}$ alkyl group. In some embodiments of the invention, R represents a straight- or branched-chain, saturated $C_{10}$, $C_{12}$, $C_{14}$, $C_{16}$ or $C_{18}$ alkyl group. In some embodiments of the invention, R represents a straight- or branched-chain, saturated $C_{10}$, $C_{12}$ or $C_{14}$ alkyl group. In some embodiments of the invention, R represents a straight- or branched-chain saturated $C_{12}$ alkyl group. In some embodiments, the at least one compound of Formula (I) of the present invention may be selected from the group consisting of laureth-6-carboxylic acid, laureth-8-carboxylic acid, laureth-11-carboxylic acid, the respective alkali metal salts thereof, or mixtures thereof. In some embodiments of the present invention the at least one compound of Formula (I) is laureth-6-carboxylic acid or an alkali metal salt thereof. In some embodiments of the present invention the at least one compound of Formula (I) is laureth-8-carboxylic acid or an alkali metal salt thereof. In some embodiments of the present invention the at least one compound of Formula (I) is laureth-11-carboxylic acid or an alkali metal salt thereof.

In some embodiments of the present invention, the at least one compound of Formula (I) or alkali metal salt thereof is present in an amount of 1.0 wt. % or more to 10.0 wt. % or less based on the weight of the entire composition. In some embodiments of the present invention, the at least one compound of Formula (I) or alkali metal salt thereof is present in an amount of 3.0 wt. % or more to 5.0 wt. % or less based on the weight of the entire composition.

In the non-aerosol shaving composition of the present invention, the compound of Formula (I) may be present as an alkali metal salt thereof. The alkali metal is selected from the group consisting of lithium, sodium and potassium. In some embodiments the alkali metal is sodium or potassium.

In some embodiments the alkali metal salt of both component (i) and component (ii) is a sodium or potassium salt. In some embodiments the alkali metal salt of both component (i) and component (ii) is a potassium salt.

In some embodiments of the present invention, the compounds encompassed by the at least one compound of general Formula (I) wherein R represents a straight- or branched-chain, saturated $C_{10}$ to $C_{18}$ alkyl group and n represents an integer between 4 and 12, constitute the only compounds of general Formula (I) in the entire non-aerosol shaving composition (irrespective of the length of the alkyl group or of the value of n). In some embodiments of the present invention, the only compounds of general Formula (I) in the entire non-aerosol shaving composition (irrespective of the length of the alkyl group or of the value of n) are the compounds in which R represents a straight- or branched-chain, saturated $C_{12}$, $C_{14}$ or $C_{16}$ alkyl group and n represents an integer between 4 and 12. In some embodiments of the present invention, the only compounds of general Formula (I) in the entire non-aerosol shaving composition (irrespective of the length of the alkyl group or of the value of n) are the compounds in which R represents a straight- or branched-chain, saturated $C_{12}$, $C_{14}$ or $C_{16}$ alkyl group and n is 6. In some embodiments of the present invention, the only compounds of general Formula (I) in the entire non-aerosol shaving composition (irrespective of the length of the alkyl group or of the value of n) are the compounds in which R represents a straight-chain, saturated $C_{12}$, $C_{14}$ or $C_{16}$ alkyl group and n is 6. In some embodiments of the present invention, the only compound of general Formula (I) in the entire non-aerosol shaving (irrespective of the length of the alkyl group or of the value of n) is the compound in which R represents a straight-chain, saturated $C_{12}$ alkyl group and n is 6.

In some embodiments of the present invention, the ratio of component (i) to component (ii) is from 3:1 to 1:3. In some embodiments, the ratio of component (i) to component (ii) is from 2:1 to 1:1. In some embodiments, the ratio of component (i) to component (ii) is 1:1.

In some embodiments of the present invention, the total amount of component (i) and component (ii) is up to 15 wt. %, based on a total weight of the composition. In some embodiments of the present invention, the total amount of component (i) and component (ii) is up to 12.5 wt. %, based on a total weight of the composition. In some embodiments of the present invention, the total amount of component (i) and component (ii) is up to 10.0 wt. %, based on a total weight of the composition.

Component (iii)

The composition of the present invention further comprises at least one polyvinyl pyrrolidone. In some embodiments of the present invention, the at least one polyvinyl pyrrolidone is present in an amount of 0.1 wt. % or more to 5.0 wt. % or less based on the weight of the entire composition. In some embodiments of the present invention, the at least one polyvinyl pyrrolidone is present in an amount of 1.0 wt. % or more to 3.0 wt. % or less based on the weight of the entire composition.

In some embodiments of the invention, the at least one polyvinyl pyrrolidone has a number average molecular weight of 100,000 Daltons or more to 2,000,000 Daltons or less. In some embodiments of the invention, the polyvinyl pyrrolidone has a number average molecular weight of 300,000 Daltons or more to 1,550,000 Daltons or less. In some embodiments of the invention, the polyvinyl pyrrolidone has a number average molecular weight of 900,000 Daltons or more to 1,500,000 Daltons or less.

Component (iv)

The composition of the present invention further comprises water, i.e., it is an aqueous composition. It is an embodiment of the present invention wherein the non-aerosol shaving composition is substantially oil-free. However, vegetable oils such as cotton seed oil, olive oil, tsubaki oil, coconut oil, soybean oil, sesame oil, cacao butter and/or castor oil may be incorporated therein to provide additional moisturization benefits or enhance skin feel. Preferably, water is present in a quantity sufficient to bring the total weight of the shaving composition to 100.0 g or similar scale.

Alternative Embodiments

In some embodiments of the present invention the at least two $C_{14}$ to $C_{18}$ carboxylic acids (i) are a $C_{14}$ carboxylic acid and a $C_{16}$ carboxylic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a $C_{14}$ carboxylic acid and a $C_{18}$ carboxylic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a $C_{16}$ carboxylic acid and a $C_{18}$ carboxylic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a $C_{14}$ carboxylic acid, a $C_{16}$ carboxylic acid, and a $C_{18}$ carboxylic acid, and the compound of Formula (I) is laureth-6-carbolic acid.

In some embodiments of the present invention the at least two $C_{14}$ to $C_{18}$ carboxylic acids (i) are a $C_{14}$ carboxylic acid, a $C_{18}$ carboxylic acid, and a $C_{18}$ carboxylic acid, and the compound of Formula (I) is laureth-6-carbolic acid.

In some embodiments of the present invention the at least two $C_{14}$ to $C_{18}$ carboxylic acids (i) are a $C_{16}$ carboxylic acid, a $C_{18}$ carboxylic acid, and a $C_{18}$ carboxylic acid, and the compound of Formula (I) is laureth-6-carboxylic acid.

In some embodiments of the present invention the at least two $C_{14}$ to $C_{18}$ carboxylic acids (i) are a combination of myristic acid and palmitic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and stearic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of palmitic acid and stearic acid, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{16}$ carboxylic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and palmitic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{16}$ carboxylic acid in a ratio of 3:1 to 1:3, and in the compound of Formula (I), R represents a saturated, straight- or branched-chain $C_{12}$ alkyl group and n is 6.

In some embodiments of the present invent on the at least two $C_{14}$ to $C_{18}$ carboxylic acids (i) are a combination of myristic acid and palmitic acid in a ratio of 3:1 to 1:3, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{16}$ carboxylic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and palmitic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{16}$ carboxylic acid in a ratio of 1:1, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and palmitic acid in a ratio of 1:1, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{18}$ carboxylic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and stearic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{18}$ carboxylic acid in a ratio of 3:1 to 1:3, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and stearic acid in a ratio of 3:1 to 1:3, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{18}$ carboxylic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and stearic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ and a $C_{18}$ carboxylic acid in a ratio of 1:1, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid and stearic acid in a ratio of 1:1, and in the compound of Formula (I). R represents a saturated, straight- or branched-chain $C_{12}$ alkyl group and n is 6.

In some embodiments of the present invention the at least two $C_{14}$ to $C_{18}$ carboxylic acids (i) are a combination of a $C_{16}$ and a $C_{18}$ carboxylic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of palmitic acid and stearic acid in a ratio of 5:1 to 1:5, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{16}$ and a $C_{18}$ carboxylic acid in a ratio of 3:1 to 1:3, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of palmitic acid and stearic acid in a ratio of 3:1 to 1:3, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{16}$ and a $C_{18}$ carboxylic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of palmitic acid and stearic acid in a ratio of 2:1 to 1:2, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of a $C_{16}$ and a $C_{18}$ carboxylic acid in a ratio of 1:1, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of palmitic acid and stearic acid in a ratio of 1:1, and in the compound of Formula (I). R represents a saturated, straight- or branched-chain $C_{12}$ alkyl group and n is 6.

In some embodiments of the present invention the at least two $C_{14}$ to $C_{18}$ carboxylic acids (i) are a combination of a $C_{14}$ carboxylic acid, a $C_{18}$ carboxylic acid, and a $C_{18}$ carboxylic acid in a ratio of 1:1:1, and in the compound of Formula (I), R represents a saturated, straight- or branched-chain $C_{12}$ alkyl group and n is 6.

In some embodiments of the present invention the at least two $C_{14}$ to $C_{18}$ carboxylic acids (i) are a combination of myristic acid, palmitic acid and stearic acid in a ratio of 1:1:1, and in the compound of Formula (I), R represents a saturated, straight- or branched-chain $C_{12}$ alkyl group and n is 6.

In some embodiments, the composition of the invention comprises 2.0 wt. % or more to 15.0 wt. % or less of a combination of myristic acid and palmitic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof. 3.0 wt. % or more to 10.0 wt. % or less laureth-6-carboxylic acid or an alkali metal salt thereof, 1.0 wt. % or more to 3.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof in a ratio of 5:1 to 1:5, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof in a ratio of 3:1 to 1:3, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof in a ratio of 2:1 to 1:2, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof in a ratio of 1:1, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof, 3.0 wt. % or more to 10.0 wt. % or less laureth-6-carboxylic acid or an alkali metal salt thereof, 1.0 wt. % or more to 3.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof in a ratio of 5:1 to 1:5, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof in a ratio of 3:1 to 1:3, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof in a ratio of 2:1 to 1:2, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and stearic acid or alkali metal salts thereof in a ratio of 1:1, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof, 3.0 wt. % or more to 10.0 wt. % or less laureth-6-carboxylic acid or an alkali metal salt thereof, 1.0 wt. % or more to 3.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof in a ratio of 5:1 to 1:5, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof in a ratio of 3:1 to 1:3, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof in a ratio of 2:1 to 1:2, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of palmitic acid and stearic acid or alkali metal salts thereof in a ratio of 1:1, 1.0 wt. % or more to 15.0 wt. % or less laureth-6-carboxylic acid or an alkali metal salt thereof, 1.0 wt. % or more to 5.0 wt. % or less of a polyvinyl pyrrolidone and water.

In some embodiments, the composition of the invention comprises 2.0 wt. % or more to 15.0 wt. % or less of a combination of myristic acid and palmitic acid or alkali metal salts thereof, 1.0 wt. % or more to 15.0 wt. % or as laureth-6-carboxylic acid or an alkali metal salt thereof, 1.0 wt. % or more to 5.0 wt. % or less of a polyvinyl pyrrolidone, and water wherein the ratio of the combination of myristic acid and palmitic acid or alkali metal salts thereof to the laureth-6-carboxylic acid or an alkali metal salt thereof is in ratio of 2:1 to 1:2.

In some embodiments, the composition of the invention comprises 2.0 wt. % or more to 15.0 wt. % or less of a combination of myristic acid and palmitic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone, and water wherein the ratio of the combination of myristic acid and palmitic acid or alkali metal salts thereof to the laureth-6-carboxylic acid or an alkali metal salt thereof is in ratio of 1:1.

In some embodiments, the composition of the invention comprises 2.0 wt. % or more to 15.0 wt. % or less of a combination of myristic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone, and water wherein the ratio of the combination of myristic acid and stearic acid or alkali metal salts thereof to the laureth-6-carboxylic acid or an alkali metal salt thereof is in ratio of 2:1 to 1:2.

In some embodiments, the composition of the invention comprises 2.0 wt. % or more to 15.0 wt. % or less of a combination of myristic acid and stearic acid or alkali metal salts thereof, 1.0 wt. % or more to 15.0 wt. % or less laureth-6-carboxylic acid or an alkali metes salt thereof, 1.0 wt. % or more to 5.0 wt. % or less of a polyvinyl pyrrolidone, and water wherein the ratio of the combination of myristic acid and stearic acid or alkali metal salts thereof to the laureth-6-carboxylic acid or an alkali metal seat thereof is in ratio of 1:1.

In some embodiments, the composition of the invention comprises 2.0 wt. % or more to 15.0 wt. % or less of a combination of palmitic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone, and water wherein the ratio of the combination of palmitic acid and stearic acid or alkali metal salts thereof to the laureth-6-carboxylic acid or an alkali metal salt thereof is in ratio of 2:1 to 1:2.

In some embodiments, the composition of the invention comprises 2.0 wt. % or more to 15.0 wt. % or less of a combination of palmitic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone, and water wherein the ratio of the combination of palmitic acid and stearic acid or alkali metal salts thereof to the laureth-6-carboxylic acid or an alkali metal salt thereof is in ratio of 1:1.

In some embodiments, the composition of the invention comprises 2.0 wt. % or more to 15.0 wt. % or less of a combination of myristic acid, palmitic acid and stearic acid or alkali metal salts thereof, 1.0 wt. % or more to 15.0 wt. % or less laureth-6-carboxylic acid or an alkali metal salt thereof, 1.0 wt. % or more to 5.0 wt. % or less of a polyvinyl pyrrolidone, and water wherein the ratio of the combination of myristic acid, palmitic acid and stearic acid or alkali metal salts thereof to the laureth-6-carboxylic acid or an alkali metal salt thereof is in ratio of 1:1.

pH of the Composition

It is desirable that the composition of the present invention have a pH value within a specific range. In one embodiment, the composition of the invention has a pH value of 9 or more to 10 or less. In a further embodiment, the composition of the present invention has a pH value of 9.3 or more to 9.8 or less. The basic pH allows the acids used herein to remain substantially solubilized in the final formulation. Cloudy compositions at an acceptable pH level may also be acceptable if other criteria such as foam quality and shave quality are acceptable.

In some embodiments of the invention, the non-aerosol shaving composition may further comprise additional agents, additional ingredients or combinations thereof. The nature of these additives is explained hereinafter.

Additional Agents

The propellant-free composition of the invention may optionally further comprise at least two additional agents selected from the group comprising polyethylene glycols, polyquaternium polymers, linear or cyclic polyalcohols such as glycerine, ethylene glycol, propylene glycol, sorbitol, xylitol, mannitol, phytantriol, pentaerythritol, inositol, or combinations thereof. When the composition of the present invention comprises at least four said additional agent, the identity of said additional agents is different to that of any of components (i), (ii), (iii), and (iv) described above.

In one embodiment of the present invention, the propellant-free composition further comprises a polyethylene glycol. The polyethylene glycol provides an enhanced skin feel and glide while helping to stabilize the foam. In one embodiment of the invention, the polyethylene glycol has an average molecular weight of 3,000 to 10,000 Daltons. In one embodiment of the invention, the polyethylene glycol has an average molecular whether of 5,000 to 7,000 Daltons.

In one embodiment of the present invention, the non-aerosol shaving composition further comprises one or more polyquaternium polymers. Included in the list of polyquaterniums which may be used as at least two additional agent comprised in the composition of the invention are Polyquaternium-1, Polyguaternium-2, Polyquaternium-4, Polyquaternium-5, Polyguaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-38, Polyquaternium-39, Polyquaternium-42, Polyquaternium-45, Polyquaternium-46, Polyquaternium-47 or combinations thereof.

Polyquaternium polymers may be used in the composition of the present invention to fulfill one or a number of roles including that of an anti-microbial agent. The polyquaternium polymers, being positively charged, are also a skin adhesion promoter since human skin is negatively charged. It provides good skin feel to the shaving composition for a superior shaving experience.

In one embodiment of the invention, said additional agent is present in an amount of 0.1 wt. % or more to 1.0 wt. % or less based on the weight of the entire composition. In one embodiment of the invention, said additional agent is present in an amount of 0.1 wt, % to 0.5 wt. %.

Additional Ingredients

In addition to the aforementioned constituents and optional additional agents, the composition of the present invention may further comprise an additional ingredient selected from the group comprising conditioning agents, moisturizing agents, anti-microbial agents, preservatives, stabilizers, cleansing agents, pH-adjusting agents, anti-freezing agents, emulsifiers, and combinations thereof. When the composition of the present invention comprises at least two said additional ingredient, the identity of said ingredient is different to that of any of components (i), (ii), (iii) and (iv) or of any of the additional agents respectively described above.

The composition of the present invention is also largely neutral in scent and thus is well suited to combination with perfumes and scents to impart distinctive, easily-controlled fragrances to the composition. In this respect, any suitable scents and fragrances known to the skilled person may be combined with the composition of the invention.

When the composition of the present invention comprises at least two additional ingredients, said additional agent may be present in any amount which allows for the realization of the desired primary effect of the additional agent whilst not preventing the realization of the effect(s) conferred by the combination of the essential ingredients (i) to (iv) in solving the problem(s) underlying the present invention. Care must also be used in choosing such additional agents so that the viscosity of the final formulation does not exceed a viscosity that allows the non-aerosol shaving composition to be used in a hand operated pump to generate the foam. In some embodiments, the viscosity of the non-aerosol shaving composition is 500 to 800 cPs. In some embodiments the viscosity of the non-aerosol shaving composition is 600 to 700 cPs.

Conditioning Agents

Non-limiting examples of conditioning agents may include skin conditioning agents such as exfoliating agents and emollients/moisturizing agents including vitamin precursors and derivatives such as, for example, vitamins A, C and E, aloe, allantoin, panthenol, alpha-hydroxy acids, beta-hydroxy acids, phospholipids, triglycerides, botanical oils and amino acids.

Emollients/Humectants/Moisturizing Agents

Suitable emollients may include mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example, methoxypolyethylene glycol (MPEG); polyalkylene glycols; linear and/or cyclic polyalcohols; lanolin and lanolin derivatives; mixtures thereof, and the like. Silicone fluids (e.g., volatile silicone oils and non-volatile silicone oils as described above), can also serve as emollients. Humectants such as glycerine, propylene glycol, sorbitol, phytantriol, panthenol, allantoin, or combinations thereof, are also useful.

Mineral oils and petrolatums include cosmetic, USP and NF grades and are commercially available from Penreco under the Drakeol® and Penreco® trade names. Mineral oils include hexadecane and paraffin oil.

Suitable fatty alcohol emollients include fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Exemplary of the fatty acid and fatty alcohol ester emollients include hexyl laurate, decyl oleate, isopropyl stearate, isopropyl isostearate, butyl stearate, octyl stearate, cetyl stearate, myristyl myristate, octyldodecyl stearoyl stearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohol emollients are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect, the ethoxylated fatty alcohols can be represented by the formula R'—$(OCH_2CH_2)_{n'}$—OH, wherein R' represents the aliphatic residue of the parent fatty alcohol and n represents the number of molecules of ethylene oxide. In another aspect, R' is derived from a fatty alcohol containing 8 to 30 carbon atoms. In one aspect, n' is an integer ranging from 2 to 50, 3 to 25 in another aspect, and 3 to 10 in a further aspect. In a still further aspect, R' is derived from a fatty alcohol emollient set forth above. Exemplary ethoxylated fatty alcohols include capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. The propoxylated adducts of the foregoing fatty alcohols and mixed ethoxylated/propoxylated adducts of the foregoing fatty alcohols are also contemplated. The ethylene oxide and propylene oxide units of the ethoxylated/propoxylated fatty alcohols can be arranged in random or in blocky order.

More specific examples of ethoxylated alcohols include Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10, Specific examples of propoxylated alcohols include PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols include PPG-1 Beheneth-15, PPG-12 Capryleth-18, PPG-2-Ceteareth-9, PPG-4-Ceteareth-12. PPG-10-Ceteareth-20, PPG-1-Ceteth-1, PPG-1-Ceteth-5, PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1 PPG-8-Ceteth-2, PPG-8-Ceteth-5, PPG-8-Ceteth-I O, PPG-8-Ceteth-20, PPG-2 $C_{12-13}$ Pareth-8. PPG-2 $C_{12-15}$ Pareth-6, PPG-4 $C_{13-15}$ Pareth-15, PPG-5 $C_{9-15}$ Pareth-6. PPG-6 $C_{9-11}$ Pareth-5, PPG-6 $C_{12-15}$ Pareth-12, PPG-6 $C_{12-18}$ Pareth-11 PPG-3 $C_{12-14}$ Sec-Pareth-7, PPG-4 $C_{12-14}$ Sec-Pareth-5, PPG-5 $C_{12-14}$ Sec-Pareth-7, PPG-5 $C_{12-14}$ Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4-Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-1 1, PPG-20-PEG-20 Hydrogenated Lanolin, PPG-2-PEG-1 1 Hydrogenated Lauryl Alcohol Ether. PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4. PPG-34-Steareth-3, PPG-38 Steareth-6, PPG-1 Trideceth-6, PPG-4 Trideceth-6, and PPG-6 Trideceth-8.

Preservatives/Anti-Microbial Agents

In one aspect, any preservative suitable for use in personal care products can be used in the exemplary compositions. Suitable preservatives include polymethoxy bicyclic oxazolidine, methyl paraben, propyl paraben, ethyl paraben, butyl paraben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzoisothiazolinone, triclosan, and suitable polyquaternium compounds disclosed above (e.g., Polyquaternium-1) may also have anti-microbial properties.

pH Adjusting Agents

The pH of the exemplary compositions can be adjusted with any combination of acidic and/or basic pH adjusting agents to provide a pH of 9 or more to 10 or less. Preferably the pH of the final composition is between 9 to 9.5, more preferably, between 9 to 9.25. It is also contemplated that the basic pH of the final formulation, i.e., pH of 9 or more to 10 or less, may provide an inhospitable environment for microbial growth such that additional preservatives and/or antimicrobial agents are not necessary.

Examples of inorganic bases which can be used to increase the pH include alkali metal hydroxides (especially sodium, potassium), and ammonium hydroxide, alkali metal salts of inorganic acids, such as sodium borate (borax), sodium phosphate, sodium pyrophosphate, and the like, and mixtures thereof. Examples of organic bases which can be used to increase the pH include triethanolamine (TEA), diisopropanolamine, triisopropanolamine, aminomethyl propanol, dodecylamine, cocamine, oleamine, morpholine, triamylamine, triethylamine, tetrakis(hydroxypropyl)ethylenediamine, L-arginine, aminomethyl propanol, tromethamine (2-amino-2-hydroxymethyl-1,3-propanediol), and PEG-15 cocamine. Alternatively, other alkaline materials can be used alone or in combination with the above mentioned inorganic and organic bases.

Acidic materials suitable for decreasing the pH include organic acids and inorganic acids, for example, acetic acid, citric acid, tartaric acid, alpha-hydroxy acids, beta-hydroxy acids, salicylic acid, lactic acid, glycolic acid, and natural fruit acids, or inorganic acids, for example, hydrochloric acid, nitric acid, sulfuric acid, sulfamic acid, phosphoric acid, and combinations thereof. A combination of acidic and basic pH adjusting agents may be employed.

Buffering agents can be used in the exemplary compositions. Suitable buffering agents include alkali or alkali earth metal carbonates, phosphates, bicarbonates, citrates, borates, acetates, acid anhydrides, succinates, and the like, such as sodium phosphate, sodium citrate, sodium acetate, sodium bicarbonate, and sodium carbonate.

The pH adjusting agent and/or buffering agent is utilized in a quantity sufficient to obtain and/or maintain a desired pH value in the composition. During manufacture, the pH adjusting agent assists in substantially solubilizing component (i) and component (ii).

Rheology Modifiers

The composition may further contain one or more rheology modifiers to reduce the viscosity of the non-aerosol shaving composition. A comprehensive list of rheology modifying chemicals useful in the present invention can be found in the International Cosmetic Ingredient Dictionary and Handbook (T. Gottschalk and H. P. Breslawec, "International Cosmetic Ingredient Dictionary and Handbook" pages 3974-3977, 14$^{th}$ Edition, Personal Care Products Council Publisher, Washington, D.C., USA (2012)), which is hereby incorporated by reference.

The present invention further relates to a method of making the composition of the invention, wherein the method comprises the steps
  (a) combining at least the components (i), (ii), (iii) and (iv); and
  (b) mixing said components.

For example, the components (i) and (ii) are dispersed in a sufficient amount of water as a single phase and heated to about 90° C. under reflux conditions. A base, i.e., potassium hydroxide, is added to deprotonate components (i) and (ii) to increase their solubility. Components (iii) and (iv) can be added and when the dispersion is substantially transparent either before or after cooling the dispersion to room temperature. The pH is then adjusted to the desired range with a strong acid while still maintaining a transparent mixture. A desired pH range is 9.0 to less than 10.0, with a maximum of 9.5 being most preferred. In some embodiments, additional agents such as polyethylene glycol, polyalcohols, and the polyquaternium polymers may be added prior to cooling and/or final pH adjustment.

The present invention also relates to a container containing the non-aerosol shaving composition of the invention. In some embodiments, the container further comprises a dispensing mechanism. In this regard, all common dispensing mechanisms known to the person skilled in the art are suitable for use with the container of the invention. In some embodiments, the dispensing mechanism is a hand-operated pump mechanism. The container may comprise a reservoir capable of containing the non-aerosol shaving composition of the invention. In some embodiments the container comprises a suction inlet capable of introducing a quantity of external air into the container while preventing the entry of water or other external liquids into the container. The container of the present invention is not pressurized and need not be sealed. The container of the present invention can be made from any suitable material including plastics, in particular recyclable plastics such as PET. The container of the present invention may also be transparent such to allow the consumer to observe the remaining quantity of the shaving composition held therein. The container of the present invention is typically made from a material whose surface can be easily modified by the addition of, for example, decorations, graphic illustrations, labels and the like. Examples of suitable containers can be found in US Patent Application No. 2013/0048755 and U.S. Pat. No. 4,880,161.

A preferred container provides a desired composition to air ratio of 90:10 to 95:5 to provide the particular fine pored, white and creamy foam composition desired by consumers. The output per stroke should be 0.5 ml to 1.5 ml, and preferably between 0.6 ml to 0.75 ml per stroke. Upon rubbing onto one's skin, the foam maintains the fine pores and is constantly converted into creaminess similar to that found in a post-foaming gel shaving composition. The liquid constituents are mixed in the foaming chamber of the pump and is discharged through a nylon mesh of 100/200, and preferably with a mesh 150/250. The neck finish size of a preferred foam pump is 40 to 43 mm.

The present invention further relates to a shaving foam obtainable from the composition of the invention, to the use of the composition of the invention as a foamable shaving composition and for shaving and to the use of the shaving foam obtained from the composition of the invention for shaving.

Examples

Methods and Materials

Components (i) and (ii) were placed in a flask with water and 1.3 to 3.5 wt. % potassium hydroxide with stirring under reflux conditions for two (2) hours. After cooling to 30° C., the pH was adjusted with hydrochloric acid to 9.5. Remaining components (iii) and (iv) were premixed together and added to the flask with polyethylene glycol in an amount of 0.2 wt. %, polyquaternium-7 was added in an amount of 0.1 wt. %, perfume was added in an amount of 0.4 wt. %. Glycerine was added in an amount of 1.0 wt. % and propylenglycol was added in an amount of 0.25 wt. %. Mixing continued until the mixture was transparent to the human eye.

The mixture was placed in a container fitted with a Model F2 pump with the L11 engine from Albéa Alkmaar, France. The container dispensed 0.75 mL of foam. Foam that converted into a dense, fine pored, very creamy, white foam after rubbing on the skin that lasted more than 5 minutes (similar to a conventional aerosol foam) was deemed exceptional. Foam that converted to a creamy, white foam after rubbing on the skin and that lasted for at least 3 minutes was deemed acceptable.

Male subjects were provided with inventive compositions to determine shave quality on the face. An exceptional shave was one that was on par with a shave using conventional aerosol foam with good glide, good skin feel, and a close shave. An acceptable shave provided only a close shave with little to no positive shaving skin attributes.

TABLE I

| Components | Ex. 1 | Ex. 2 | Ex. 3 | Ex. 4 | Ex. 5 | Ex. 6 | Ex. 7 | Ex. 8 |
|---|---|---|---|---|---|---|---|---|
| (i) $C_{12}$ Lauric Acid | | | | | | | | |
| (i) $C_{14}$ Myristic Acid | 3.330 | 1.665 | 2.500 | 3.330 | 2.500 | 1.667 | 4.167 | 5.000 |
| (i) $C_{16}$ Palmitic Acid | 1.665 | 3.330 | 2.500 | 1.665 | 1.250 | 0.833 | 2.083 | 2.500 |
| (i) $C_{18}$ Stearic Acid | | | | | | | | |
| (ii) Laureth-6-carboxylic acid | 5.000 | 5.000 | 5.000 | 2.500 | 3.750 | 2.500 | 6.250 | 7.500 |
| (iii) Polyvinylpyrrolidone | 3.000 | 3.000 | 3.000 | 3.000 | 3.000 | 3.000 | 3.000 | 3.000 |
| (iv) Water | q.s. | q.s. | q.s. | q.s. | q.s. | q.s. | q.s. | q.s. |
| Foam/Shave Quality | | | | | | | | |
| Solution quality | ✓✓ | ✓ | ✓✓ | ✓✓ | ✓✓ | ✓ | ✓✓ | ✓✓ |
| Shave quality | ++ | ++ | + | + | + | ++ | ++ | ++ |
| Foam quality | ** | ** | * | * | -- | -- | ** | ** |

| Components | Ex. 9 | Ex. 10 | Ex. 11 | Ex. 12 | Ex. 13 | Ex. 14 | Ex. 15 | Ex. 16 |
|---|---|---|---|---|---|---|---|---|
| (i) $C_{12}$ Lauric Acid | 3.330 | | 3.330 | 3.330 | | 1.665 | 1.665 | 1.665 |
| (i) $C_{14}$ Myristic Acid | 1.665 | | | | 3.330 | 1.665 | 1.665 | |
| (i) $C_{16}$ Palmitic Acid | | 3.330 | | 1.665 | | 1.665 | | 1.665 |
| (i) $C_{18}$ Stearic Acid | | 1.665 | 1.665 | | 1.665 | | 1.665 | 1.665 |
| (ii) Laureth-6-carboxylic acid | 5.000 | 5.000 | 5.000 | 5.000 | 5.000 | 5.00 | 5.000 | 5.000 |
| (iii) Polyvinylpyrrolidone | 3.000 | 3.000 | 3.000 | 3.000 | 3.000 | 3.000 | 3.000 | 3.000 |
| (iv) Water | q.s. | q.s. | q.s. | q.s. | q.s. | q.s. | q.s. | q.s. |
| Foam/Shave Quality | | | | | | | | |
| Solution quality | -- | ✓ | -- | -- | ✓ | -- | ✓✓ | ✓✓ |
| Shave quality | -- | ++ | -- | -- | ++ | -- | -- | + |
| Foam quality | -- | ** | -- | -- | ** | -- | -- | * |

| Components | Ex. 17 | Ex. 18 | Comp A | Comp B | Comp C | Comp D |
|---|---|---|---|---|---|---|
| (i) $C_{12}$ Lauric Acid | | 1.250 | 5.000 | | | |
| (i) $C_{14}$ Myristic Acid | 1.665 | 1.250 | | 5.000 | | |
| (i) $C_{16}$ Palmitic Acid | 1.665 | 1.250 | | | 5.000 | |
| (i) $C_{18}$ Stearic Acid | 1.665 | 1.250 | | | | 5.000 |
| (ii) Laureth-6-carboxylic acid | 5.000 | 5.000 | 5.000 | 5.000 | 5.000 | 5.000 |
| (iii) Polyvinylpyrrolidone | 3.000 | 3.000 | 3.000 | 3.000 | 3.000 | 3.000 |
| (iv) Water | q.s. | q.s. | q.s. | q.s. | q.s. | q.s. |
| Foam/Shave Quality | | | | | | |
| Solution quality | ✓ | ✓ | ✓✓ | ✓✓ | -- | -- |
| Shave quality | ++ | + | -- | + | + | -- |
| Foam quality | ** | * | -- | -- | -- | -- |

-- unacceptable
✓ cloudy solution
✓✓ transparent solution
+ acceptable shave
++ exceptional shave
* acceptable foam
** exceptional foam Examples 1, 7, and 8 demonstrated the most desirable properties, namely, a transparent solution with exceptional shave quality and foam quality. Examples 10, 13, and 17 yielded slightly cloudy solutions with no precipitate with exceptional shave quality and foam quality. A consumer packaged product may require a container that is not transparent if consumers are bothered by a solution that is cloudy. These examples demonstrate the upper and lower amounts of the total amount of both component (i) and component (ii), in the inventive compositions with the most preferred ratio of the at least two $C_{14}$ to $C_{18}$ carboxylic acids, and the most preferred ratio of component (i) to component (ii).

Comparative examples A to D show the criticality of the at least two carboxylic acids of component (i). None of the comparative examples having a single $C_{14}$ to $C_{18}$ carboxylic acid performed on par with conventional aerosol shaving compositions.

While the invention has been described in detail herein in accordance with certain preferred embodiments thereof, many modifications and changes therein may be affected by those skilled in the art without departing from the spirit of the invention. Accordingly, it is our intent to be limited only by the scope of the appending claims and not by way of the details and instrumentalities describing the embodiments shown herein.

The invention claimed is:

1. A propellant-free composition comprising:
   (i) two or more carboxylic acids including at least one $C_{14}$ carboxylic acid or alkali metal salt thereof, present in an amount of about 1.6 wt. % to about 5.0 wt. %, based on the weight of the entire composition, and at least one $C_{16}$ to $C_{18}$ carboxylic acid or alkali metal salt thereof and excluding a $C_{12}$ carboxylic acid comprising lauric acid or alkali metal salt thereof, wherein a ratio of the at least one $C_{14}$ carboxylic acid or alkali metal salt thereof to one of the at least one $C_{16}$ to $C_{18}$ carboxylic acid or alkali metal salt thereof is from about 1:2 to about 2:1;

(ii) at least one compound of general Formula (I):

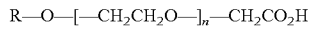

or alkali metal salt thereof, wherein R represents a straight- or branched-chain, saturated $C_{10}$ to $C_{18}$ alkyl group, n represents an integer between 4 and 12, and the at least one compound of general Formula (I) is present in an amount of about 2.5 wt. % to about 10.0 wt. %, based on the weight of the entire composition;

(iii) polyvinyl pyrrolidone; and (iv) water.

2. The composition according to claim 1, wherein the at least one $C_{14}$ carboxylic acid or alkali metal salt thereof and/or the at least one $C_{16}$ to $C_{18}$ carboxylic acid or alkali metal salt thereof is a straight-chain fatty acid.

3. The composition according to claim 1, wherein the at least one $C_{14}$ carboxylic acid comprises myristic acid or alkali metal salt thereof, the at least one $C_{16}$ carboxylic acid comprises palmitic acid or alkali metal salt thereof, the at least one $C_{18}$ carboxylic acid comprises stearic acid or alkali metal salt thereof, and the $C_{12}$ carboxylic acid is lauric acid or alkali metal salt thereof.

4. The composition according to claim 1, wherein in the at least one compound of general Formula (I), n is 5.

5. The composition according to claim 4, wherein n is 6 to 8.

6. The composition according to claim 1, wherein R in the at least one compound of general Formula (I) represents a straight- or branched-chain, saturated $C_{10}$, $C_{12}$, $C_{14}$, $C_{16}$ or $C_{18}$ alkyl group.

7. The composition according to claim 6, wherein R in the at least one compound of general Formula (I) represents a straight- or branched-chain, saturated $C_{10}$, $C_{12}$ or $C_{14}$ alkyl group.

8. The composition according to claim 6, wherein R in the at least one compound of general Formula (I) represents a straight- or branched-chain, saturated $C_{12}$ alkyl group.

9. The composition according to claim 6, wherein R in the at least one compound of general Formula (I) represents a straight-chain, saturated $C_{12}$ alkyl group.

10. The composition according to claim 1, wherein the at least one $C_{14}$ carboxylic acid or alkali metal salt thereof and the at least one $C_{16}$ to $C_{18}$ carboxylic acid or alkali metal salt thereof are present in an amount of about 2.0 wt. % to about 10.0 wt. %, based on the weight of the entire composition.

11. The composition according to claim 10, wherein the at least one $C_{14}$ carboxylic acid or alkali metal salt thereof and the at least one $C_{16}$ to $C_{18}$ carboxylic acid or alkali metal salt thereof are present in an amount of about 2.0 wt. % to about 7.5 wt. %, based on the weight of the entire composition.

12. The composition according to claim 1, wherein the at least one compound of general Formula (I) is present in an amount from about 5.0 wt. % to about 10.0 wt. %, based on the weight of the entire composition.

13. The composition according to claim 1, wherein the at least one compound of general Formula (I) is present in an amount of about 5.0 wt. %, based on the weight of the entire composition.

14. The composition according to claim 1, wherein the polyvinyl pyrrolidone is present in an amount of 0.1 wt. % or more to 5.0 wt. % or less, based on the weight of the entire composition.

15. The composition according to claim 14, wherein the polyvinyl pyrrolidone is present in an amount of 1.0 wt. % or more to 3.0 wt. % or less, based on the weight of the entire composition, and wherein the polyvinyl pyrrolidone has a number average molecular weight of 100,000 Daltons or more to 2,000,000 Daltons or less.

16. A propellant-free composition comprising:

(i) two or more carboxylic acids including at least one $C_{16}$ carboxylic acid or alkali metal salt thereof, present in an amount of about 1.6 wt. % to about 3.3 wt. %, based on the weight of the entire composition, and at least one $C_{18}$ carboxylic acid or alkali metal salt thereof and excluding a combination of a $C_{12}$ carboxylic acid comprising lauric acid or alkali metal salt thereof and a $C_{14}$ carboxylic acid or alkali metal salt thereof comprising myristic acid or alkali metal salt thereof, wherein a ratio of the at least one $C_{16}$ carboxylic acid to the at least one $C_{18}$ carboxylic acid is from about 1:2 to about 2:1;

(ii) at least one compound of general Formula (I):

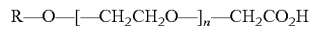

or alkali metal salt thereof, wherein R represents a straight- or branched-chain, saturated $C_{10}$ to $C_{18}$ alkyl group, n represents an integer between 4 and 12, and the at least one compound of general Formula (I) is present in an amount of about 2.5 wt. % to about 10.0 wt. %, based on the weight of the entire composition;

(iii) polyvinyl pyrrolidone; and (iv) water.

17. The composition according to claim 16, wherein the ratio of the at least one $C_{16}$ carboxylic acid to the at least one $C_{18}$ carboxylic acid is from about 1:1 to about 2:1.

18. The composition according to claim 16, wherein the ratio of the at least one $C_{16}$ carboxylic acid to the at least one $C_{18}$ carboxylic acid is about 1:1.

19. The composition according to claim 16, wherein the ratio of the at least one $C_{16}$ carboxylic acid to the at least one $C_{18}$ carboxylic acid is about 2:1.

20. The composition according to claim 16, said composition further comprising additional ingredients selected from the group consisting of conditioning agents, moisturizing agents, humectants, anti-freezing agents, anti-static agents, anti-microbial agents, preservatives, stabilizers, cleansing agents, pH-adjusting agents, thickeners, emulsifiers, cationic surfactants, zwitterionic surfactants, non-ionic surfactants, anionic surfactants, and combinations thereof.

21. The composition according to claim 16, said composition further comprising an additional agent selected from the group consisting of polyethylene glycols, polyalcohols, polyquaterniums, lauroyl methyl isethionates, cocamidopropyl betaines and lauroamphoacetates, or combinations thereof.

22. A composition according to claim 21, wherein said one or more additional agent is present in an amount of 0.1 wt. % or more to 1.1 wt. % or less, based on the weight of the entire composition.

23. A method of providing the composition according to claim 1, wherein said method comprising the steps of:

(a) combining at least the components (i), (ii), (iii) and (iv); and (b) mixing said components.

24. A container containing the composition of claim 1.

25. The container of claim 24, wherein said container further comprises a dispensing mechanism.

26. The container of claim 25, wherein said dispensing mechanism is a hand-operated pump mechanism.

27. The composition according to claim 16, wherein the at least one compound of general Formula (I) is present in an amount of about 5.0 wt. %, based on the weight of the entire composition.

28. The composition according to claim 16, wherein the ratio comprises palmitic acid or alkali metal salt thereof and stearic acid or alkali metal salt thereof from about 1:2 to about 2:1, and wherein the at least one compound of general Formula (I) comprises laurenth-6-carboxylic acid or alkali metal salt thereof in an amount of about 5.0 wt. %, based on the weight of the entire composition.

29. The composition according to claim 1, wherein the ratio comprises myristic acid or alkali metal salt thereof and palmitic acid or alkali metal salt thereof from about 1:2 to about 2:1, and wherein the at least one compound of general Formula (I) comprises laurenth-6-carboxylic acid or alkali metal salt thereof in an amount of about 5.0 wt. %, based on the weight of the entire composition.

* * * * *